United States Patent [19]

Hatschek

[11] Patent Number: 5,309,916
[45] Date of Patent: May 10, 1994

[54] BLOOD PRESSURE MEASURING DEVICE AND METHOD

[75] Inventor: Rudolf A. Hatschek, Fribourg, Switzerland

[73] Assignee: AVL Medical Instruments AG, Schaffhausen, Switzerland

[21] Appl. No.: 730,596

[22] Filed: Jul. 16, 1991

[30] Foreign Application Priority Data

Jul. 18, 1990 [CH] Switzerland ................ 2390/90

[51] Int. Cl.$^5$ .............................................. A61B 5/026
[52] U.S. Cl. .................... 128/672; 128/661.08
[58] Field of Search ............. 128/661.01, 661.05, 128/661.08, 661.09, 665, 667, 672, 691, 694

[56] References Cited

U.S. PATENT DOCUMENTS

| 4,296,754 | 10/1981 | Hennig et al. ................ 128/694 |
| 4,357,944 | 11/1982 | Mauser et al. |
| 4,370,985 | 2/1983 | Takeichi et al. |
| 4,562,843 | 1/1986 | Djordjevich et al. ........... 128/672 |
| 4,703,758 | 11/1987 | Omura ........................... 128/691 |
| 4,807,638 | 2/1989 | Sramek .......................... 128/672 |

(List continued on next page.)

FOREIGN PATENT DOCUMENTS

| 1905620 | 8/1970 | Fed. Rep. of Germany. |
| 2481917 | 11/1981 | France. |
| 2523432 | 9/1983 | France. |

OTHER PUBLICATIONS

Okada "Possible Determination of Pulse-Wave Velocity in Vivo", IEEE Transactions on Biomedical Engineering, vol. 35, No. 5, May 1988, pp. 357–361.
Prandtl, "Führer durch die Strömungslehre", Verlag Friedr. Vieweg & Sohn, Braunschweig, 1965, title page and pp. 472, 473.
E. R. Pike, "Laser Doppler Anemometry, a Comparative Study of the Measurement of Motion by Light Scattering" The Engineering uses of Coherent Optics, Proceedings & edited discussion of a conference held at the University of Strathclyde, Glasgow, 8–11 Apr. 1975, pp. 431–457.
Sturgill et al, "An Improved Blood Velocity Estimator Optimized for Real-Time Ultrasound Flow Applications" 1990 Ultrasonics Symposium, vol. 3, pp. 1467–1471.
Routh et al, "Preliminary Studies into High Velocity Transverse Blood Flow Measurement", 1990 Ultrasonics Symposium, vol. 3, pp. 1523–1526.

(List continued on next page.)

Primary Examiner—Lee S. Cohen
Assistant Examiner—Samuel Gilbert
Attorney, Agent, or Firm—Spencer, Frank & Schneider

[57] ABSTRACT

A device for measuring blood pressure includes a sensor arrangement which is releasably attached to the exterior of a body and which is electrically conductively connected with electronic circuit. The sensor arrangement and the circuit are configured to determine, in at least one measuring region of the body, a valve which is a measure for a variable that changes periodically over time in the rhythm of the pulse beat and which is correlated with the blood pressure. This variable may, for example, be the flow velocity and/or flow quantity and/or the volume of the arterial blood and/or a cross-sectional dimension and/or the flow cross section area of an arterial blood vessel. The sensor and circuit further determine a value which is a measure for the pulse wave velocity. By linking the two values together and including at least one calibration value, at least one value that is characteristic for of the blood pressure (preferably including at least the systolic blood. pressure) can be determined. The device makes it possible to measure the blood pressure of a person at least quasi-continuously with relatively little bother for the person.

25 Claims, 4 Drawing Sheets

U.S. PATENT DOCUMENTS

| | | | |
|---|---|---|---|
| 4,873,987 | 10/1989 | Djordjevich et al. | 128/672 |
| 4,984,567 | 1/1991 | Kageyama et al. | 128/661.05 X |
| 5,099,852 | 3/1992 | Meister | 128/691 X |
| 5,111,817 | 5/1992 | Clark et al. | 128/672 X |
| 5,111,826 | 5/1992 | Nasiff | 128/672 |

OTHER PUBLICATIONS

Tamura et al, "Determination of 2-D Velocity Vectors using Color Doppler Ultrasound", 1990 Ultrasonics Symposium, vol. 3, pp. 1537–1540.

Bohs et al, "A Novel Method for Angle Independent Ultrasonic Imaging of Blood Flow and Tissue Motion", IEEE Transactions on Biomedical Engineering, vol. 38, No. 3, Mar. 1991, pp. 280–286.

Mohapatra et al, "The Measurement of Peripheral Blood Flow by the Electrical Impedance Technique", Journal of Medical Engineering and Technology, vol. 3, No. 3, May 1979, pp. 132–137.

Marks, "Digital Enhancement of the Peripheral Admittance Plethysmogram", IEEE Transactions on Biomedical Engineering, vol. BME-34, No. 3, Mar. 1987, pp. 192–197.

Prospectus "Moor Instruments MBF3D-Dual Channel Microvascular Laser Doppler Blood Flow Monitor", Moor Instruments, Ltd. Trinity Hill, Axminster, Devon, England, 4 pages.

BLOOD PRESSURE MEASURING DEVICE AND METHOD

BACKGROUND OF THE INVENTION

The invention relates to a device and a method for measuring blood pressure.

The device and the method serve to measure blood pressure, namely to measure blood pressure in a non-invasive manner. The term "non-invasive" here means that the measurement is performed without an instrument being introduced into a blood vessel and is thus effected with sensor means which are disposed completely outside of the living human, or possibly animal body whose blood pressure is being measured.

At present, blood pressure is mostly measured by methods based on the Riva-Rocci method. Prior art devices provided for such blood pressure measurements include a deformable cuff. This cuff defines a cavity which is connected with a compressed gas source, usually formed by a pump that pumps air, an outlet and a pressure measuring device. Means are further provided to be able to associate two values of this pressure when there is a change in the pressure existing in the cuff—namely upon deflation of the cuff—with the systolic and the diastolic pressure. The association with the systolic and the diastolic pressure can here be made either on the basis of Korotkoff sounds generated when the blood flows through an artery or according to the oscillometric variant of the method. In more recent prior art sphygmomanometers, the pressure measuring devices include a measuring transducer that is connected with the cavity in the cuff for converting the pressure into an electrical value, electronic circuit means and a display member for the analog or digital display of the systolic and diastolic blood pressure. Devices for determining the systolic and diastolic blood pressure on the basis of the Korotkoff sounds additionally include either a stethoscope or a microphone. Reference is here made, for example, to German Laid-Open Patent Application 3,014,199 and the corresponding U.S. Pat. No. 4,459,991. The pulsating flow of the blood is able to excite vibrations in the gas present in the cuff, normally air. In the devices provided for oscillometric measurements, the pressure measuring transducer and the electronic circuit means are configured to detect the fluctuations of the pressure in the cuff connected with the above-mentioned vibrations.

For a measurement according to the Riva-Rocci method, the cuff is fastened to a body segment—for example an upper arm or a finger—and is pumped up until the pressure of the air present in its cavity is sufficient to constrict the artery in the enclosed member. Then the cuff is slowly deflated. In the variant involving the detection of the Korotkoff sounds by means of a stethoscope or microphone, two values are detected and identified for the pressure in the cuff cavity during deflation of the cuff as the systolic blood pressure and the diastolic blood pressure, respectively. The pressure existing in the cuff during the first occurrence of Korotkoff sounds is associated with the systolic blood pressure. The diastolic pressure is recognized by the fact that the actual Korotkoff sounds disappear, with the sounds generated by the flowing blood becoming lower and less distinct or disappearing altogether. In the oscillometric variant of the method, the pressures of the air contained in the cuff and corresponding to the systolic and diastolic blood pressures are determined in that the fluctuations in the cuff pressure caused by the pulsating flow of the blood begin to appear or disappear again.

For seriously ill or critical accident victims and/or patients just coming out of surgery and in other cases it may be necessary or at least desirable to measure the blood pressure of the respective patient over a certain period of time—for example over several hours or days—permanently and as continuously as possible. In practice, devices are known for this purpose which operate according to the Riva-Rocci method and in which the cuff can be inflated and deflated automatically in cycles during operation, with the systolic and diastolic blood pressure each being measured during the deflation. However, periodic pumping up and subsequent deflating of the cuff and the interruption of blood circulation connected therewith in the limb around which the cuff is placed is unpleasant for the patient being examined and may even be damaging to his health. Since an inflation/deflation cycle usually requires at least about one minute and, moreover, short pauses should be introduced between successive measurements to keep annoyance to the patient being examined at a minimum, the Riva-Rocci method does not really permit truly continuous blood pressure measurements.

The publication entitled "Possible Determinants of Pulse-Wave Velocity In Vivo" by Masahiko Okada, in IEEE Transactions on Biomedical Engineering, Volume 35, No. 5, May 1988, pages 357–361, discloses a photoplethysmographic method for measuring pulse wave velocity that will be discussed in greater detail below. The measurement is made at the finger or toe tips with the use of light at a wavelength of 300 nm to 500 nm. This publication describes the correlation of the pulse wave velocity with various other parameters and variables, one of which is the blood pressure. According to this publication, a certain correlation was found to exist between the pulse wave velocity and the systolic and diastolic blood pressure. Such a relatively slight correlation, however, does not permit a determination of the blood pressure. Since the pulse wave velocity does not change periodically, it would also not be possible, in particular, to determine the systolic and the diastolic blood pressure from the pulse wave velocity. Moreover, the walls of the large arteries and the tissue portions usually covering them toward the exterior are practically impermeable to light of a wavelength of 300 nm to 500 nm. The method disclosed in the publication by M. Okada is therefore suitable only for measurements at thin-walled blood vessels near the surface, which are correspondingly small and is not suitable for measurements at large, correspondingly thick-walled blood vessels that may possibly be relatively far removed from the surface of the body part being examined.

Several general characteristics relating to blood circulation will now be discussed. The circulatory system includes arterial blood vessels -(that is, arteries),-venous blood vessels, and capillaries that interconnect the two types of vessels. The smallest arterial blood vessels or arteries, that are connected directly with the capillaries, are called arterioles. The arterial blood vessels have elastically deformable walls and are at least in part provided with muscle fibers and/or enclosed by such muscle fibers. These muscle fibers are able to compress the arteries and particularly the arterioles to different degrees and thus influence their elasticity, the flow resistance and the distribution of blood to the various blood vessels. The heart pumps the blood in a pulsating manner—that is, in surges—through the blood vessels. The blood flows through the blood vessels at a flow velocity v that is a function of locus as well as time. If, for the sake of simplification, it is initially assumed that the blood vessels have rigid walls, changes in pressure in the blood propagate at the speed of sound cs, whose second power or square is defined by the following formula:

$$c_s^2 = k/\rho \quad (1)$$

where $\rho$ is the density of the blood and K the modulus of compression, which is also called the volume elasticity modulus and is equal to the reciprocal of compressibility, usually identified as $\kappa$.

In reality, however, the arterial blood vessels do not have rigid walls but—as already mentioned—elastically deformable walls. During each blood surge caused by one cardiac cycle and the pulse-like pressure increase connected therewith, the arterial blood vessels are distended. These distensions propagate along the arterial blood vessels. The velocity at which the change in pressure caused by a cardiac cycle or blood surge propagates along an arterial blood vessel under the influence of its wall elasticity, is the already mentioned pulse wave velocity $c_{pw}$. According to the book by Ludwig Prandtl, entitled "Fürer durch die Strömungs-lehre" [Fluid Mechanics Guide], published by Verlag Friedr. Vieweg & Sohn, Braunschweig, 1965, the second power or square of the propagation velocity of pressure changes in tubes having elastically distensible walls, and thus at least approximately also the second power or square of the pulse wave velocity, neglecting flexural vibrations, is given by the following equation:

$$c_{pw}^2 = c_s^2 \, Es/(Kd + Es) \quad (2)$$

where E is the modulus of elasticity of the blood vessel wall, s is the thickness of the blood vessel wall and d is the interior diameter of the blood vessel.

According to the above-cited publication by M. Okada, the square of the pulse wave velocity is given by the following equation:

$$c_{pw}^2 = Es/d\rho \quad (3)$$

By inserting $c_s$ in Equation (2), it can be demonstrated that Equation (3) is derived from Equation (2) if, for the sake of simplicity, the second product in the parenthetical expression in Equation (2) is omitted.

The flow velocity of the blood is—as already mentioned—a function of locus as well as time. Its maximum value in an arterial blood vessel and particularly in a large artery of a grown human being is at most about 0.5 m/s and normally a little less. According to Equations (2) and (3), the pulse wave velocity is dependent upon the ratio of the wall thickness to the diameter of the arteries. Since this ratio increases from the heart toward the capillaries and since the pulse wave velocity additionally is a function of the modulus of elasticity and of the tension in the muscle fibers belonging to the respective blood vessel, the pulse wave velocity changes along the arterial blood vessels and is also dependent upon the state of the human beings or animals examined. In the arteries, the pulse wave velocity is typically about 4 m/s to 5 m/s. The speed of sound in water, which is known to be the major component of blood, lies in an order of magnitude of 1500 m/s. The pulse wave velocity $c_{pw}$ is thus significantly greater, namely at least or approximately 10 times greater, than the flow velocity v, and the speed of sound $c_s$, in turn, is very much greater than the pulse wave velocity.

The blood pressure developing in a certain blood vessel depends on the pumping output of the heart, on the flow resistance of the blood vessel, on the momentary quantity flowing through, on the elasticity of the blood vessel wall and on the viscosity of the blood.

SUMMARY OF THE INVENTION

The object of the invention is to provide a device and a method for non-invasively measuring blood pressure, with the device and method avoiding the drawbacks of the prior art devices and methods discussed above. More particularly, the object of the invention is to make it possible to monitor the blood pressure of a human being or possibly an animal essentially continuously without having to alternatingly inflate and deflate a cuff, while nevertheless attaining good measuring accuracy.

It has been found that the blood pressure can be determined relatively accurately by obtaining two different value, a first one of the volume being a variable that changes continuously in at least one measuring region periodically over time in the rhythm of the pulse beat and/or its change as a function of the pulse, while the other or, second value is a value which provides a measure for the pulse wave velocity and/or its change. By using at least one calibration value determined according to the above-described Riva-Rocci method and linking the two values together, it is possible to form at least one value which is a measure for a characteristic blood pressure value and/or its change, with it being possible to measure and display, for example, at least the systolic pressure and, for example, also the diastolic and/or the average blood pressure.

The device includes sensor means which comprise, for example, at least one sensor that is releasably fastened to a body part, with it being possible to employ two identical or two different sensors. At least the sensor or each sensor serving to measure the first, periodically changing value is preferably attached to an arm or possibly a leg. The device preferably further includes a display and monitoring unit constituted by one or several such devices and including at least part of the electronic circuit means of the device.

The mentioned first value which changes over time in synchronism with the pulse beat and also in synchronism with the blood pressure—that is, in the same rhythm as the blood pressure—is correlated with the blood pressure by way of a physical linkage, but must be formed, of course, differently from the blood pressure and not directly by the blood pressure itself or by a change in the blood pressure. The sensor means and the electronic circuit means may be configured to determine and display in the form of an electrical signal as the first value, a value that is a measure for the momentary value of the flow velocity and/or its change in synchronism with the pulse beat and/or the flow quantity and/or the volume of the blood in a measuring region and/or a cross-sectional dimension and/or the area of the passage cross section of at least one arterial blood vessel. Since the blood vessels and particularly the arteries normally have an approximately circular cross section, the mentioned or determined cross-sectional dimension may be formed at least in approximation by the interior or exterior diameter or by an average diameter of the blood vessel. In this connection, it should also be noted that the variables mentioned for the first value are closely linked with one another. If the quantity of the flow is measured in volume units per unit time, the flow quantity is equal to the product of the average flow velocity averaged over the cross-sectional area times the area of the flow passage cross section of the blood vessel.

The device may, for example, be configured to detect the flow velocity and/or the flow quantity as the first value in that lightwaves—namely monochromatic coherent lightwaves—or ultrasonic waves are directed into a body part to be examined and lightwaves or ultrasonic waves, respectively, that are scattered by the blood or—more precisely—by the blood cells are detected. The light or ultrasonic radiation may here be pulsed. In these methods which are based on the scattering of light or ultrasound, components of the flow velocity or flow quantity that are directed at a right angle and/or parallel to the direction of incidence of the light or ultrasound can be detected as desired. Various types of such measuring methods based on the scattering of light or ultrasound are known. If light is employed, the measurements may be effected, for example, with the aid of photon correlation, light beating spectroscopy, speckle interferometry or the Doppler effect. In this connection, reference is made, for example, to the publication by E. R. Pike, entitled "Laser Doppler Anemometry, a Comparative Study of the Measurement of Motion by Light Scattering", in "The Engineering Uses of Coherent Optics", "Proceedings and Edited Discussion of a Conference Held at the University of Strathclyde, Glasgow," Apr. 8-11, 1975, Cambridge University Press, pages 431-457.

If ultrasound is employed, the measurements may be done in similar ways, namely, for example, with the aid of time domain correlation, an interference speckle pattern and/or a Fourier transformation or the Doppler effect. A few such measuring methods are described, for example, in the following articles published in "Proceedings zum IEEE Ultrasonics Symposium" [Proceedings of the IEEE Ultrasonics Symposium] 1990, Volume 3: M. R. Sturgill, R. H. Love, B. K. Herres, "An Improved Blood Velocity Estimator Optimized For Real-Time Ultrasound Flow Applications", pages 1467-1471; H. F. Routh, T. L. Pusateri, D. D. Waters, "Preliminary Study Into High Velocity Transverse Blood Flow Measurement", pages 1523-1526; and T. Tamura, R. S. C. Cobbold, K. W. Johnston, "Determination of 2-D Velocity Vectors Using Color Doppler Ultrasound", pages 1537-1540. Reference is also made to the publication by L. N. Bohs, G. E. Trahey, entitled "A novel Method For Angle Independent Ultrasonic Imaging of Blood Flow and Tissue Motion", in IEEE Transactions on Biomedical Engineering, Volume 38, No. 3, 1991, pages 280-286.

Regarding the various methods based on lightwaves or ultrasonic waves, it should also be noted that these methods are sometimes identified somewhat non-uniformly by the various authors and equipment manufacturers. For example, methods in which a flow velocity is measured that occurs at a right angle to the direction of the radiation are sometimes included in the Doppler effect methods although, strictly speaking and in the classical sense, the Doppler effect is understood to mean the generation of a frequency shift by a velocity component that is parallel to the direction of propagation of the waves in a wave radiation source.

If a determination of the flow velocity and/or flow quantity by means of light is provided, the device may include one or a plurality of light sources and one or a plurality of light receivers. The or each sensor may then include, for example, at least one optoelectronic transducer serving as a light source, for example a laser light emitting diode, and at least one optoelectronic transducer serving as a light receiver, for example a photodiode or a phototransistor. These transducers may then be connected with the or a device in the display and monitoring unit by means of a flexible electrical cable. However, it is also possible to arrange at least one or each optoelectronic transducer within the mentioned unit and to connect it with a sensor by way of a flexible light conductor. In this case, the sensors then include the respective light conductor or only one end of it as the light source and/or light receiver and, for example, additionally an optical transmission element.

In an advantageous embodiment of a device for measuring the flow velocity or flow quantity with the aid of scattered light, at least one light source generates light whose wave-length lies in the near infrared range and is at least 700 nm, at most 1200 nm and, for example, 800 nm to 1000 nm. Such light is able to penetrate relatively thick layers of tissue and primarily also the walls of large arteries so that the flow velocity and/or flow quantity can be measured not only in small arteries but also in large arteries For the determination of the flow velocity and/or flow quantity with the use of ultrasound, the or each sensor may include at least one transducer which includes a piezo-electric element and constitutes the ultrasound source for the radiation of ultrasound pulses into a body part as well as an ultrasound receiver for receiving the scattered-back ultrasound.

Another possibility is to configure the device so that it is able to determine, on the basis of a measurement of the electrical impedance or admittance, a first value which is a measure for the changing volume over time of the blood present in the measuring region of a body part and/or the diameter and/or the flow passage cross section area of at least one artery lying in the measuring region and/or of the quantity of blood flowing through. The device ma include sensor means equipped with electrodes that are releasably fastened to the respective body part in a spaced relationship along a larger artery existing in the respective body part so that they enclose it at least to a major portion or, for example, completely. The device preferably includes a high frequency generator for generating an alternating voltage and supply it to at least two electrodes. The frequency of the alternating voltage may lie approximately in a range from 30 kHz to 3 MHz and is preferably at least 70 kHz, at most 150 kHz and, for example, 80 kHz to 100 kHz. For further general information regarding this variant of the measuring method, reference is made to the publication by S. N. Mohapatra, H. M. Arenson, entitled "The Measurement of Peripheral Blood Flow by the Electrical Impedance Technique", in the Journal of Medical Engineering and Technology, Volume 3, No. 3, 1979, pages 132-137, and the publication by L. A. Marks, entitled "Digital Enhancement of the Peripheral Admittance Plethysmogram", in IEEE Transactions on Biomedical Engineering, Volume BME-34, No. 3, 1987, pages 192-197.

The flow velocity of the blood can also be measured inductively by means of sensors including at least one coil. The or each coil may be releasably fastened to an arm or other body part in such a way that the coil axis extends approximately at a right angle to a large artery and preferably at least approximately intersects it.

Moreover, a value providing a measure for the diameter of a large artery can be determined as the first value in that the reflection of the ultrasound at the artery wall is evaluated. The area of the flow passage cross section of the artery can then of course also be determined from the diameter.

Various possibilities also exist for determining the pulse wave velocity and/or the change over time of the pulse wave velocity. For example, the sensor means and electronic circuit means may be configured in such a way that they determine the first value—that is, variable—which changes over time in synchronism with the pulse beat at two measuring locations or in two measuring regions that are spaced from one another along the flow path of the arterial blood, particularly along a large artery and to represent them in the form of electrical signals. Moreover, the time difference can be determined by which the time curves of the first value determined for the two measuring regions—for example the maxima of the first value—are shifted relative to one another. If the two measuring regions are at a fixed distance from one another, the pulse wave velocity is then inversely proportional to the mentioned time difference. The second value can also be represented in the form of an electrical signal and may be formed, for example, by the mentioned time difference and/or its reciprocal value and/or directly by the pulse wave velocity.

The pulse waves generated by a heart propagate away from it along arterial blood vessels to the capillaries and are reflected there with a more or less greatly reduced amplitude. As will now be explained, this reflection of the pulse waves makes it possible to derive, from the time sequence of the first value measured in a single measuring region, a second value which is a measure for the pulse wave velocity. A pulse wave traveling away from the heart along an artery will hereinafter be called the primary pulse wave. Since a large artery—such as the one in the arm or leg—is normally connected with capillaries through several branches along its length, pulse waves reflected by various capillaries are able to return to the mentioned large artery and may there be superposed to form a larger reflected pulse wave which, in turn, is superposed on the primary pulse wave and thus interferes with it. The difference in phase between the primary pulse wave and the reflected pulse wave resulting at a certain measuring location is a function of the pulse wave velocity and of the distance of the capillaries causing the reflection from the measuring region. If the measuring region is disposed at an arm, the reflection occurs primarily at the many capillaries existing in the hand so that the mentioned phase difference is determined decisively by the distance of the hand from the measuring region. If a measurement is made at a leg, the distance of the foot from the measuring region is analogously decisive for the difference in phase. The curve representing the blood pressure over time has a primary maximum in each period whose value is equal to the systolic blood pressure and a smaller secondary maximum which is caused by the interference between a primary and a reflected pulse wave and which is more or less distinct. In the technical language, this secondary maximum is called a dicrotic notch. Moreover, the dicrotic notch is always disposed in the descending portion of the blood pressure curve, that is, between a systolic blood pressure value and the subsequent diastolic blood pressure value. The flow velocity and the other stated variables which may constitute the first value to be measured, become greater with increasing blood pressure and lower with decreasing blood pressure. Accordingly, for each cardiac cycle, the time curves of the variable mentioned as the first value have a primary extreme, namely the primary maximum associated with the systolic pressure, and a secondary extreme, namely a secondary maximum, associated with the dicrotic notch, and between them a relative intermediate minimum. The time or phase shift between a primary extreme and the timely adjacent, subsequent secondary extreme is a function of the difference in phase between the primary pulse wave and the reflected pulse wave and thus also of the pulse wave velocity. The sensor means and the circuit means may therefore be configured so as to form, in one measuring region, from the time curve of the variable determined for the first value, a second value in the form of the time difference and/or phase angle difference between the primary extreme and an adjacent, subsequent extreme, namely the secondary maximum, or possibly the intermediate minimum, and to represent it in the form of an electrical signal.

Another possibility of determining the pulse wave velocity is to configure the sensor means and the electronic circuit means in such a way that they detect in one measuring region one of the variables mentioned as the first value and additionally, analogously to electrocardiography, at least one current of the cardiac muscle and to determine the so-called R wave of the cardiogram in which the systole occurs—that is, the contraction of the cardiac muscle—and the blood is expelled from the heart. As already described, during the pulse period, the flow velocity or other variable forming the first value has a maximum which occurs at the same time as the systolic blood pressure. The device may therefore be further configured to determine the time difference between certain, predetermined points of the curves that occur once during each pulse period and which represent the time sequences of the cardiac muscle current and of the variable measured as the first-mentioned value. For example, the time difference between the R wave of the cardiac muscle current curve and the point in time at which the first value has its maximum during a pulse period can be determined. This time difference or its change and/or a value linked to this time difference and its change may then serve as the second value which provides a measure for the pulse wave velocity and its change.

BRIEF DESCRIPTION OF THE DRAWINGS

The subject matter of the invention will now be described in greater detail with reference to embodiments thereof that are illustrated in the drawing figures. In the drawing figures.

DESCRIPTION OF THE PREFERRED EMBODIMENTS

Figure 1:
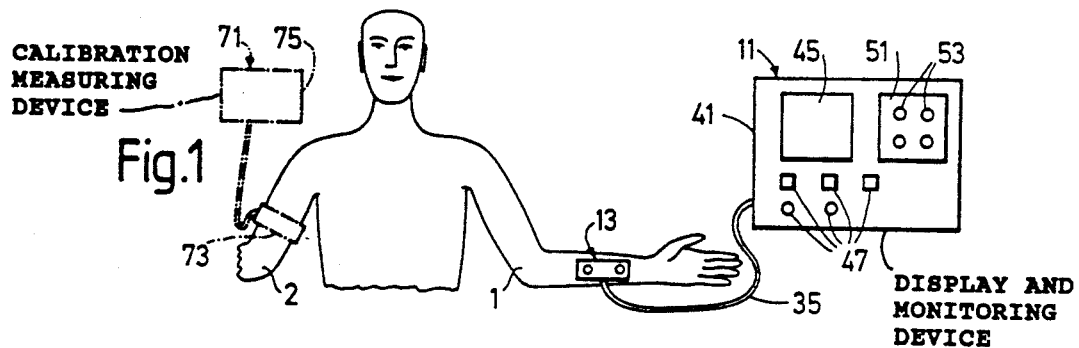
FIG. 1 is a schematic front view of a sphygmomanometer employing sensor means that are disposed at the arm of a person.
Figure 2:
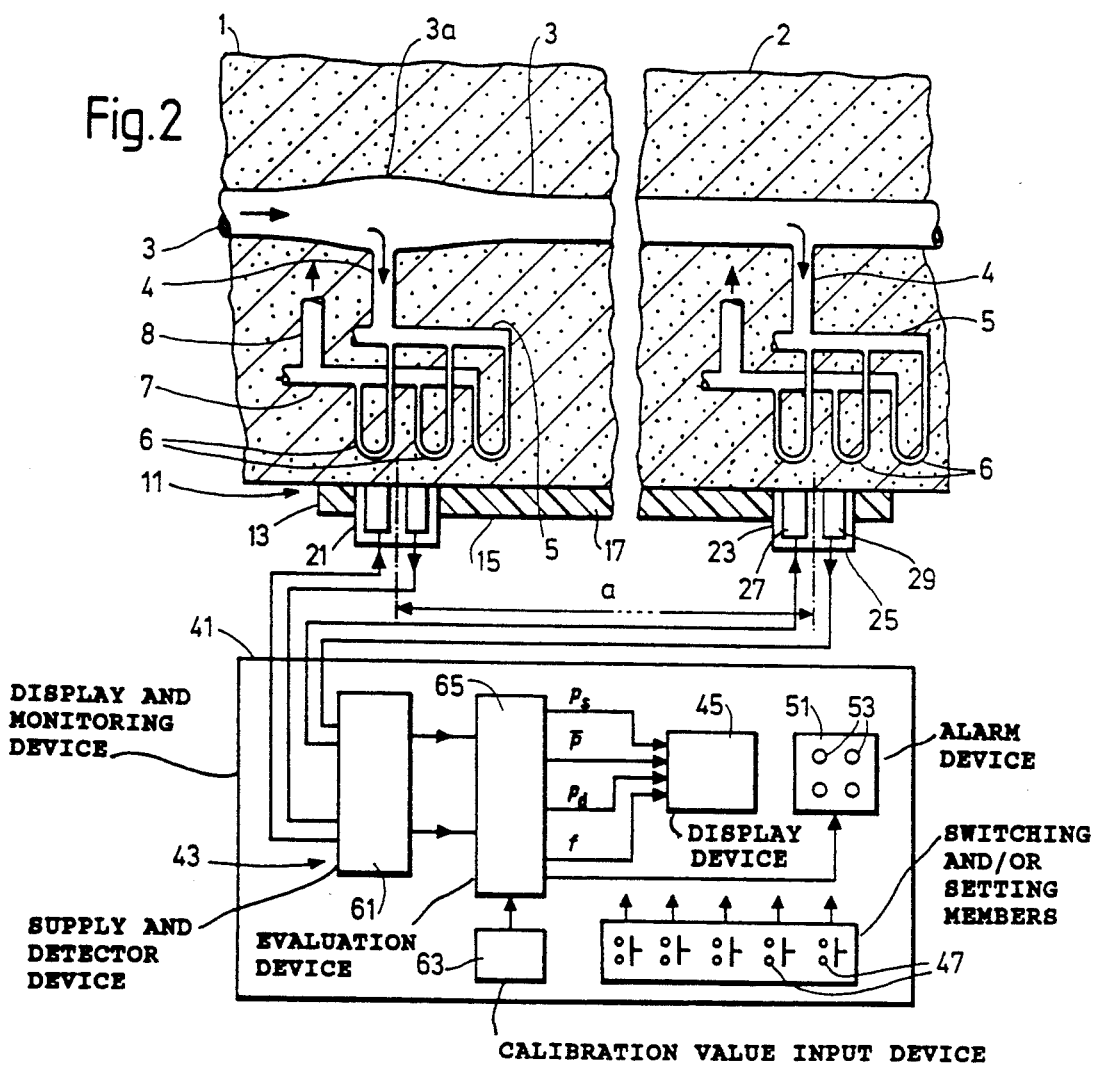
FIG. 2 is a schematic longitudinal sectional view of segments of the arm and of sensor means including a light source and a light receiver fastened to the arm as well as a block circuit diagram of the electronic circuit mean of the device.

FIG. 1 shows a body part 1, namely an arm 1 on a living human body. The arm 1, part of which is also shown in FIG. 2 in a schematic and simplified representation, includes blood vessels. These comprise a large artery 3 extending along the entire arm of which sections of the arteria radialis lying in the forearm are shown in the drawing and which is progressively distended at 3a due to a surge of blood. By way of smaller arteries 4 and arterioles 5 distributed and branching off along it, artery 3 is connected with 6 at one end of the capillaries. A particularly large number of arterioles exist which are disposed near the body surface in and/or underneath the skin and extend at least approximately parallel to the skin. The ends of capillaries 6 not connected with arterioles 5 are connected with larger veins 8 by way of venules 7.

A device 11 shown in FIGS. 1 and 2 serves to measure blood pressure and pulse rate and is provided with sensor means 13 that are disposed on the exterior of arm 1—namely at the forearm. These sensor means include a holder 15 that is releasably fastened to arm 1 and is composed of an elongate, plate or strip-shaped holding member 17, made, for example, of a not very flexible, electrically insulating plastic. The longitudinal direction of the holding body lies approximately parallel to that of the arm and contacts it at one side. Holder 15 may be releasably fastened, for example, by means of releasable adhesive connecting means (not shown) that are disposed approximately between the arm 1 and holding member 17. These adhesive means may include a double-sided adhesive strip and/or at least one adhesive strip disposed on the exterior of holder 15 and glued to it as well as to the arm. Instead of adhesive connecting means, holder 15 may also be equipped with a cuff that surrounds arm 1 and is provided with a hook-and-loop closure or some other type of closure.

Holder 15 holds a first sensor 21 and a second sensor 23. The two sensors 21, 23 are spaced from one another in the longitudinal direction of arm 1 and of artery 3 and are fastened releasably or non-releasably, perhaps glued, to holding member 17. Each sensor 21, 23 includes a housing 25 (which may, for example, be essentially cylindrical) in which at least one light source 27 and at least one light receiver 29 are disposed. The light sources 27 and light receivers 29 of the two sensors each include an optoelectronic transducer, namely a laser light emitting diode or a photodiode. In operation, the laser light emitting diodes of the light sources generate coherent, monochromatic light whose wave-length is 780 to 820 nm and is, for example, approximately 810 nm. As already explained in the introduction, such light, which lies in the near infrared range, is able to penetrate the tissue of the arm and the walls of all arteries present in arm 1—; in particular, the light is able to penetrate the wall of the large artery 3. The light sources 27 of the two sensors 21, 23 are arranged in such a manner that their radiation axes—that is, the center axes of the lightwave bundles radiated into arm 1—extend approximately at a right angle to the surface and to the longitudinal direction of arm 1 and artery 3. The light receivers 29 are also arranged in such a way that they are able to receive light exiting from the arm at approximately a right angle to the surface of arm 1. Sensors 21, 23 may each be formed, for example, of sensors including a light source and a light receiver, as furnished by Moor Instruments, Ltd., Devon, Great Britain, for the dual-channel blood flow monitors produced by this firm as type MBF3D. Sensors 21, 23 may here be arranged in such a way that the radiation axes either intersect the large artery 3 or they do not.

The distance between the two sensors 21 and 23 marked "a" in FIG. 2, is preferably at least 3 cm. Particularly if the light sources are not oriented toward the large artery 3, it is of advantage to have a relatively large distance mounting to, for example, at least or approximately 6 cm. If the two sensors according to FIG. 1 are placed at the forearm, the distance a may be, for example, up to about 10 cm or possibly even up to about 15 cm. However, it must be inserted here that it is also possible to fasten the one sensor to the upper arm and the other sensor to the forearm, in which case the distance measured along the extended arm may even be greater than the above-given values. The two sensors 21, 23 have a diameter that is, for example, about 7 mm and an axial dimension that lies in the order of magnitude of 5 mm. Thus, sensor means 13 require little space, have a low weight and, in contrast to the devices operating according to the Riva-Rocci method, do not include a cuff that must be inflated and deflated or other components that must be deformed and/or moved during the measuring process to be described in detail below, so that they bother the patient to whom they are attached only slightly.

The two sensors 21, 23 of sensor means 13 are electrically connected by means of an electrical cable 35 with a display and monitoring unit or device 41 disposed at a distance from the person being examined on a table or on the console of a bed frame. The display and monitoring unit includes an instrument having a housing, but could also be constituted of several instruments in separate housings. The unit 41 includes electronic circuit means 43 which are disposed in and/or at the housing, are connected according to the block diagram shown in FIG. 2, and include at least one display unit or device 45 for the digital and/or analog display of various measured values as well as switching and/or setting members 47 that are manually operated, for example pushed and/or turned and/or flipped. Moreover, an alarm unit or device 51 is provided which includes at least one optical alarm signal generator 53, and preferably with several such alarm signal generators composed, for example, of light emitting diodes and/or lamps. Alarm unit 51 may further include at least one acoustic alarm signal generator and/or may be electrically connected with such an acoustic alarm signal generator. If the device is employed in a hospital, it may further be provided that the units 41 of several devices are able to transmit, by way of electrical conductors or in a wireless manner, alarm signals and possibly measured values to a central monitoring and alarm unit which includes optical and/or acoustical alarm signal generators.

The electronic circuit means 43 include an supply and detector unit or device 61 which is electrically connected with the optoelectronic transducers of light sources 27 and light receivers 29 of the two sensors 21, 23. This detector unit includes at least on excitation voltage source composed, for example, of a pulse generator so as to generate at least one excitation voltage in the form of, for example, a pulse sequence and to feed it to the light sources 27 so that the latter are able to radiate light—for example light pulses—into the arm. When the device is in use, light reflected by or—more precisely—scattered back from the blood cells of the arterial blood flowing through arm 1 reaches light receivers 29, whose transducers convert this light into electrical signals. The supply and detector unit 61 further includes circuit means for determining, on the basis of the scattered-back light, the flow velocities of the pulsating arterial blood in the measuring regions of arm 1 covered by the two sensors 21, 23. Unit 61 may then form electrical signals or values which, in analog or digital form, are a measure for the momentary values of the mentioned flow velocities of the blood. The supply and detector unit 61 may determine the flow velocities in the same manner or similarly to the way it is described in the literature cited in the introduction for light beams oriented transversely to the direction of flow. Moreover, unit 61 may, for example, have the same or a similar configuration as the circuit in the already mentioned dual-channel blood flow monitors available as type MBF3D from Moor Instruments, Ltd.

The display and monitoring unit also includes a calibration value input unit or device 63 equipped with electronic circuit means which are connected with..at least one of the manually operated switching and/or setting members 47.

Supply and detector, unit 61 is connected with an evaluation unit or device 65 and, during measuring, supplies it with the mentioned electrical signals or values which are a measure for the flow velocities at sensors 21, 23. The calibration value input unit 63 is also connected with evaluation unit or device 65 to supply it, during calibration, with calibration values in the form of electrical signals or values represented in analog or digital form. Evaluation unit 65 preferably includes a microprocessor, at least one memory for the storage of digitally represented data and, if required, analog/digital and/or digital/analog converters. Evaluation unit 65 has outputs that are connected with display unit 45 and with alarm unit 51. It should be noted in this connection that the separation of the electronic circuit means 43 as shown in the block circuit diagram of FIG. 2 into three function blocks—that is, units or devices 61, 63 and 65—is merely schematic and that it is possible, for example, that certain parts of these blocks or units are formed by one and the same integrated circuit and/or by one and the same microprocessor.

Let us now describe in greater detail a few aspects of the measuring process. As already mentioned, during operation of the device, light reflected or scattered back by the cells of the arterial blood reaches the light receivers 29 of both sensors 21, 23 In addition to the light reflected by the arterial blood, light that was scattered by venous blood or by tissue or by some other components of arm 1 may also enter the light receivers. However, only the light scattered by the pulsating arterial blood varies over time in the rhythm of the pulse beat, so supply and detector unit 61 is able to filter out the pulsating light component or to detect, it in same other way and to determine the flow velocity of the arterial blood from it.

As already discussed in the introduction, the pulsating pumping of the blood causes periodic changes in blood pressure over time which are synchronous with the pulse beat and which propagate at the pulse wave velocity. Each pressure maximum produced as a result of a cardiac cycle is connected with a maximum in flow velocity and causes the already mentioned distension $3a$ of artery 3 which progresses along artery 3 in the direction of blood flow at the pulse wave velocity $c_{pw}$. The flow direction of the blood and the propagation direction of the pressure change as well as distension $3a$ are marked by arrows in FIG. 2. The distension or—more precisely—its maximum, first passes the first sensor 21 and then, after a travel period $T_a$, it passes the second sensor 23, which is disposed at a distance a from the first sensor. Correspondingly, the flow velocity maxima at the two sensors for artery 3 are shifted in time relative to one another by travel time $T_a$. As mentioned, the two sensors may be arranged in such a manner that the light bundles generated by their light sources cross the large artery 3. In this situation, light reflected from the blood flowing through artery 3 is able to reach the light receivers. In such a case, the flow velocity of the blood flowing through artery 3 can be determined directly. Under this condition and under the condition that the segment of artery 3 disposed between the two sensors 21, 23 is linear and parallel to a straight line that connects the centers of the faces of the two sensors lying against the arm, the pulse wave velocity can be calculated according to the following equation:

$$c_{pw} = a/T_a \qquad (4)$$

In reality, artery 3 is normally not precisely parallel to the mentioned connection line between the sensors. But, nevertheless, the pulse wave velocity is still inversely proportional to travel time $T_a$.

As mentioned, the sensors may also be arranged in such a way that the light bundles radiated into arm 1 do not cross the large artery 3 but instead cross only smaller arterial blood vessels, particularly arterioles 5 that are more or less parallel to the surface of the arm. Since these arterioles are connected with the large artery 3 by way of relatively short, small arteries 4, the time curve of the pulse wave in arterioles 5 is shifted only relatively slightly with respect to the time curve of the pulse wave in those sections of large artery 3 which are disposed in the measuring regions where the sensors are located. At least if distance a is selected to be large enough that the arterioles present in the measuring regions of the two sensors are connected with artery 3 through branches that are spaced from one another along artery 3, the pulse wave velocity is then also determined at least approximately by Equation (4) and is in any case still proportional to the reciprocal value of the travel time $T_a$.

Evaluation circuit 65 is constructed so as to determine the travel time $T_a$ from the two signal sequences supplied to it by supply and detector unit 65 and to generate an electrical (preferably a digital) signal which is a measure for the pulse wave velocity. From the measured values determined by means of the two sensors, the relative values of two variables can thus be determined and represented by electrical signals. One of these variables is a measure for the flow velocity at one of the two sensors 21, 23 and the other is a measure for the pulse wave velocity in artery 3. Since the flow velocity varies in the rhythm of the pulse beat, the electronic circuit means 43 are also able to determine the pulse rate. Moreover, the circuit means may be configured to possibly also determine the amplitude value or the average over time of the pulsating flow velocity and to represent it in the form of on display unit 45. Moreover, the circuit means may, for example, also form the average of the amplitude values or averages over time for the flow velocities measured by the two sensors.

For the performance of a continuous blood pressure measurement, device 11 is calibrated with the aid of an additional calibrating measuring unit or device 71 which is employed only temporarily and only during a comparatively short time compared to the entire measuring duration. This unit or device 71 is shown in dash-dot lines in FIG. 1. It includes an inflatable cuff 73 as well as a measuring device 75 connected therewith and is configured to measure the blood pressure according to the Riva-Rocci method. For calibration, cuff 73, once sensor means 13 are fastened to arm 1, is temporarily attached to a part of the body, namely the upper portion of the other arm 2. In this connection, it must be noted that cuff 73 and sensor means 13 should preferably not be disposed along the sam blood flow path because the constriction of the blood flow by the cuff, and the after-effects of the constriction which exist for a certain time after removal of the cuff, may produce measuring errors. With the aid of a switching and/or setting member 47, the display and monitoring unit 41 of device 11 is caused to change to the calibration mode, that is, to an operating mode provided for calibration, while simultaneously measuring, in one of the ways described above, the systolic blood pressure ps as well as the diastolic blood pressure $p_d$ and possibly certain intermediate blood pressure values by means of the additional calibration measuring unit 71 which operates according to the Riva-Rocci method. These calibration values obtained by the calibration measuring unit are then put in manually into evaluation circuit 65 by means of at least one of the switching and/or setting members 47 through calibration value input unit 63. However, it is also possible to configure display and monitoring unit 41 and calibration measuring unit 71 in such a way that during calibration the two units 41 and 71 can be temporarily connected with one another by way of a cable and plug-in connections. In that case, it may further be provided that the calibration measuring unit 71 of unit 41 supplies at least part of the calibration values required to calibrate device 11 automatically in the form of electrical signals. After device 11 has been calibrated in one way or the other, cuff 73 of calibration measuring unit 71 can be removed again from arm 2, while sensor means 13 remain attached to arm 1 until the end of the scheduled measuring period.

If the measurement extends over a relatively long period of time—for example, over several days—device 11 may be recalibrated from time to time—for example once a day—with the aid of calibration measuring unit 71.

It shall now be described how the blood pressure can be determined from the measured values for flow velocity and pulse wave velocity and from the calibration values. In this connection, it is initially assumed that the blood vessel being measured is a circularly cylindrical tube having a rigid wall. According to the Hagen-Poiseuille theorem, the flow quantity Q, measured in volume units per unit time, through a tube having a rigid wall, an internal radius r and a length L, with laminar flow, is given by the following equation:

$$Q = p_L r^4 \pi / 8 L \eta \tag{5}$$

where $p_L$ is the pressure difference existing in a tube section having a length L and $\eta$ is the coefficient of dynamic viscosity.

If the values appearing in Equation (5) on both sides of the equal sign are divided by the inner or flow cross section area F of the blood vessel which has initially been assumed to be a rigid-walled tube, the following results for the flow velocity:

$$v = p_L r^2 / 8 L \eta \tag{6}$$

Under the simplifying assumption that the blood vessels have rigid walls, the momentary blood pressure p is proportional to the pressure difference $p_L$ and thus, according to Equations (5) and (6), proportional to the momentary flow quantity Q and to the momentary flow velocity v. Under the stated assumption and under the condition that the viscosity of the blood remains constant during a measurement, the blood pressure p can be linked with the flow velocity v and this can be expressed by the following equation:

$$p = v k_v / r^2 \tag{7}$$

where $k_v$ is a constant. If the blood vessel walls are rigid as assumed, $r^2$ is also constant. The then likewise constant quotient $k_v/r^2$ is likewise constant and could be determined during calibration. In order to determine the blood pressure, it would then merely be necessary to measure the flow velocity v and multiply it, according to Equation (7), with the mentioned quotient.

As discussed above, however, the walls of the arterial blood vessels in reality are elastically distensible so that, if there is a rise in pressure, the inner radius r as well as the flow cross section area of the blood vessels is increased in addition to the flow velocity of the blood.

If one assumes a blood vessel to be a tube having an elastically distensible wall, the relative expansion $\epsilon$ of the circumference and of the diameter is given by the following equation:

$$\epsilon = [p(2-\mu) d^2] / E (D^2 - d^2) \tag{8}$$

where $\mu$ is the Poisson number of the blood vessel wall and D the outer diameter of the blood vessel.

The expansion of a blood vessel is thus a function of the ratio of the blood pressure p to the modulus of elasticity E. Of course, conversely, the distension and thus the blood pressure are also a function of the modulus of elasticity. For example, a reduction in distensibility—with the conveying output of the heart remaining constant—results in a rise in blood pressure. The inner radius r and the modulus of elasticity E of the blood vessel walls depend on the type of blood vessels covered by the measurement, on the individual anatomical configuration of the person being examined and also on the physiologic state of the blood vessels. For example, the modulus of elasticity of a young athlete is lower than that of a old person suffering from arteriosclerosis. Moreover, the inner radius and/or the modulus of elasticity ma change relatively quickly during the measuring period. Such a change may be brought about, for example, due to a change in the tension of the muscle fibers belonging to the artery wall. The tension of muscle fibers belonging to arterial blood vessels may change, for example, if temporarily a larger portion of the blood stream is directed to the digestive organs to aid digestion or if the perfusion of the skin changes to adapt it to changes in ambient temperature. Moreover, the tension in the mentioned muscle fibers may also be influenced by the activity and the mood of the person being examined. The modulus of elasticity E of the blood vessel walls, however, is linked, according to Equation (2) or (3), with the pulse wave velocity $c_{pw}$. The pulse wave velocity or a value derived therefrom therefore is a measure for the relative value of the modulus of elasticity.

If v changes, $r^2$ in Equation (7), in deviation from the previous assumption, is in reality not constant but changes as well. Since the pulse wave velocity $c_{pw}$ measured in addition to the flow velocity V, according to Equation (2) or (3), is a measure for the modulus of elasticity E, evaluation unit 65 is able to consider the influence of the elasticity in an evaluation of the measured values v and $c_{pw}$.

Comparison measurements were made in which the device according to the invention was employed simultaneously to measure the flow velocity v as well as the pulse wave velocity $c_{pw}$ and calibration measuring unit 71 was employed to measure the blood pressure according to the Riva-Rocci method. According to these comparative measurements, a very close correlation exists, if the pulse wave velocity $c_{pw}$ remains constant, between the blood pressure p and the flow velocity v and also the flow quantity Q. If, however, the pulse wave velocity changes, the linkage of the blood pressure with the flow velocity also changes.

Thus, at a certain constant pulse wave velocity, each value of v has a value of p unequivocally associated with it. If the pulse wave velocity changes, this also causes a change in the linkage between v and p. However, for any desired, but unchanging value of the pulse wave velocity, this still results in an unequivocal linkage between v and p.

As already mentioned, evaluation unit 65 is able to calculate, from the measured values supplied to it in the form of electrical signals by excitation and detector circuit 61, a measure for the momentary flow velocities and/or flow quantities at sensors 21, 23 and a relative value for the pulse wave velocity. From the measured values determined during pulse wave velocity measurements it is possible, if required, to calculate a value which is a measure for the modulus of elasticity. Evaluation unit 65 is configured in such a way as to link values formed from the put-in calibration values and from values for the two measured variables—that is the flow velocity and/or the flow quantity and the pulse wave velocity—in a predetermined manner so that a value is formed and represented by an electrical signal which is a measure for at least one characteristic blood pressure value, preferably including the particularly important systolic blood pressure $p_s$. Evaluation unit 65 may also generate for example, electrical signals which are a measure for the average blood pressure $\bar{p}$ determined over the time of a pulse period duration and/or for the diastolic blood pressure pd. Additionally, evaluation unit 65 preferably generates an electrical signal which is a measure for the pulse rate f.

Evaluation unit 65 is able to determine the blood pressure in different ways from the measured values for flow velocity and pulse wave velocity. A few such possibilities will now be described. For example, the blood pressure p may be expressed by the following equation:

$$p = k_1 f_1(v, c_{pw}) + p_1 \qquad (9)$$

where $k_1$ and $p_1$ are each a constant and $f_1(v, c_{pw})$ is a function dependent on the two variables v and $c_{pw}$. The term "function" is here understood in a very general sense and is intended to include any association rules determined in any desired form for a function value that is associated with each pair of discrete values or value ranges of the independent variables v and $c_{pw}$. For example, on the basis of the above-mentioned comparison measurements, a table may be compiled which associates a value the function $f_1$ with every value or value range of variables v and $c_{pw}$ lying within the intended measuring range. This table can be stored, either during or after manufacture of the device, in a memory—for example a ROM memory [read-only-memory]—of the evaluation unit and then remains in effect for all measurements to be performed.

Since the calibration requires only a short period of time, the pulse wave velocity normally remains constant during the calibration process. It is thus possible during calibration, on the one hand, to measure the values of the systolic and diastolic blood pressure by means of calibration measuring unit 71 and, on the other hand, by means of the device 11 according to the invention, at least approximately simultaneously, for example during the same cardiac cycle, to measure the values for flow velocity v associated with the two blood pressure values at the momentarily existing pulse wave velocity. The blood pressure values measured by calibration measuring unit 71 can be fed by means of calibration value input unit 63 to the evaluation unit 65, which determines the two constants $k_1$ and $p_1$ and then stores them in an erasable memory until the next calibration. The evaluation unit, moreover, may be configured and/or programmed to associate a value of the function $f_1(v, c_{pw})$ from the stored table with the values of v and $c_{pw}$ and calculate the momentary blood pressure from these values according to Equation (9).

The flow velocity v and the pulse wave velocity $c_{pw}$ may be designated first and second variables, respectively. These variables can have a plurality of possible values. A value measured by one of the sensors 21, 23 and giving a measure for v may be designated a measurement value for the first variable. A value measured for $c_{pw}$ may be designated a measurement value for the second variable. The values stored in the table for the function $f_1(v, c_{pw})$ may be designated function values or table values.

It has, moreover, been found that the function $f_1(v, c_{pw})$ can be split, in a good approximation, into a product of two functions $g_1(v)$ and $h_1(c_{pw})$, of which the first function depends only on v and the second only on $c_{pw}$. Thus, the blood pressure can also be expressed in approximation by the following equation:

$$p = k_1 g_1(v) \, h_1(c_{pw}) + p_1 \qquad (10)$$

Instead of determining and storing, during the comparison measurements, the values of function $f_1$ which depend on two variables, it is also possible to determine, in the comparison measurements, the values of the two functions $g_1(v)$ and $h_1(c_{pw})$ for various values of v and $c_{pw}$, respectively, and to store them in the form of a table. The evaluation unit can then perform a measurement by calling up from the stored table a function or table value for the function $g_1(v)$ and $h_1(c_{pw})$, respectively, associated with the values measured for v and $c_{pw}$ and calculate the blood pressure p according to Equation (10).

Additionally it is possible to derive, by means of a mathematical approximation method—that is, a compensation or regression calculation—a "concrete" function representing the previously only abstractly defined function $f_1$, or at least one of the functions $g_1$, $h_1$, from the data obtained in the comparison measurements. A "concrete" function is here understood to mean a function or equation which results in a calculation rule, such as for example a power series, for calculating the function values. The microprocessor of the evaluation unit may then be programmed in such a manner that, with the aid of the mentioned calculating rule, it is able to calculate the values of the respective function from the measured values for v and/or $c_{pw}$. If the evaluation is made on the basis of Equation (10), either the values of both functions $g_1$, $h_1$ can be calculated according to a calculating rule or the values of one of the two functions $f_1$, $g_1$ can be called up from a stored table and only the values of the other function are calculated according to a calculating rule. As already mentioned, if the blood vessels had rigid walls, p would be proportional to v. Therefore, the values of variable v can possibly be used as values for a function $g_1(v)$ and thus $g_1(v)$ can be replaced by v in Equation (10).

It is also possible, on the basis of theory or by combining theoretical derivations with the results of comparison measurements, to derive other concrete formulas containing two constants determined by calibration. Of course, one can also attempt to express the linkage between the blood pressure p and variables v and $c_{pw}$, instead of by Equations (9) or (10), by a formula which contains only a single constant that is determined by calibration.

As already mentioned, it is possible, on the other hand, to measure during the calibration process, in addition to the values for the systolic and the diastolic blood pressure, at least one intermediate value that lies between these blood pressure values and to employ it as the calibration value. Moreover, it is also possible to measure, by means of device 11, the flow velocity value v corresponding to this or each blood pressure intermediate value. Then it is possible to express the linkage of blood pressure p with the measured variable values v and $c_{pw}$ by means of equations that contain three or even more constants determined by calibration.

It should also be noted in this connection that the evaluation circuit is able to determine the diastolic blood pressure "directly" from the calibration values and from the measured values or "indirectly" from the likewise picked up, average blood pressure. The average blood pressure p, which is averaged over time for the duration of a pulse period, is linked with the systolic blood pressure $p_S$ and with the diastolic blood pressure $p_d$. According to experimental tests, the linkage can be expressed by the following equation:

$$\bar{p} = p_d + (p_s - p_d) / k \qquad (11)$$

By revising this equation, the following equation results for the diastolic pressure:

$$p_d = (k \bar{p} - p_s) / (k - 1) \qquad (12)$$

In both these equations, k is an integer that depends on the body region selected as the measuring region but is at least approximately constant over time and has an approximate value of 2 for central arterial blood vessels, that is, those lying near the heart in the flow path, and a value of 3 for peripheral arterial blood vessels, that is, those that lie relatively far removed from the heart along the flow path. For the large artery 3 of the arm, k has a value that lies between 2 and 3 but closer to 2.

In the indirect method, the average blood pressure $\bar{p}$ and the systolic blood pressure $p_s$ are determined first. Then, using Equation (12), the diastolic blood pressure is calculated from $\bar{p}$ and ps. Depending on the selected measuring location, the value of the integer k included in Equations (11) and (12) may, for example, be put in manually or may possibly be determined automatically by evaluation unit 65 from put-in blood pressure calibration values and from measured values derived by device 11 during the calibration mode. The "indirect" determination of the diastolic blood pressure may possibly be of advantage, for example, in order to reduce falsifications of the measured diastolic blood pressure value due to the zero point drift phenomena.

According to Equations (5) and (6), the ratio between the flow quantity and the pressure in a flow through a rigid-walled tube, and thus of course also in the flow through a blood vessel, is also dependent on the viscosity. The viscosity coefficient of blood, however, normally changes at most slightly and slowly over time. If the device is calibrated, for example, once daily, the viscosity coefficient remains practically constant during measuring intervals lying between successive calibrations. However, the viscosity coefficient may possibly be changed by certain medical treatments. If such treatments are taking place, it may be provided that device 11 be recalibrated after each such treatment. As will be explained below, the device may also be constructed to additionally determine a value which is a measure for the viscosity and, for example, for the relative value of the already mentioned dynamic viscosity coefficient $\eta$ and/or the relative value of the kinematic viscosity coefficient $\nu$.

During measurements, display unit 45 displays the determined values for the systolic blood pressure $p_s$, the average blood pressure $\bar{p}$ and/or the diastolic blood pressure $p_d$ as well as the pulse rate f and possibly also other values. In this connection it should be noted that device 11 is able to newly determine and indicate the various values for blood pressure and possibly also the value for the pulse rate, for each cardiac cycle or pulse beat. However, device 11 may instead average the values of $p_s$, $\bar{p}$, $p_d$ and f over time for the duration of several cardiac cycles or pulse beats and display these time averaged values. Display unit 45 may be configured so as to simultaneously and continuously display several values—for example $p_s$, $\bar{p}$, $p_d$, f. However, it may also be provided that the display device displays the various displayable values or some of them only alternatingly. In the latter case, actuation of, for example, at least one of the switching and/or adjusting members permits a selection as to which one of several possible values is to be displayed.

The switching and/or adjusting members 47 also permit the setting of at least one cutoff value. For example, device 11 may be configured so as to enable an operator to put in at least one lower and one upper cutoff value for the systolic blood pressure and for the pulse rate. Evaluation unit 65 of device 11 is then able to compare, during the measurement, the continuously newly determined values of $p_s$ and f with predetermined cutoff values and to generate an appropriate electrical signal if a cutoff value is exceeded or not reached and to feed such signal to alarm unit 51 and, if required, to the possibly additionally provided central monitoring and alarm unit. A value which exceeds or falls below the respective cutoff value is then signalled by an associated optical alarm signal generator 53 to alarm unit 51 and possibly to other optical and/or acoustic alarm signal generators that may be provided. Moreover, the values determined for blood pressure and pulse rate can be stored and/or recorded.

Figure 3:
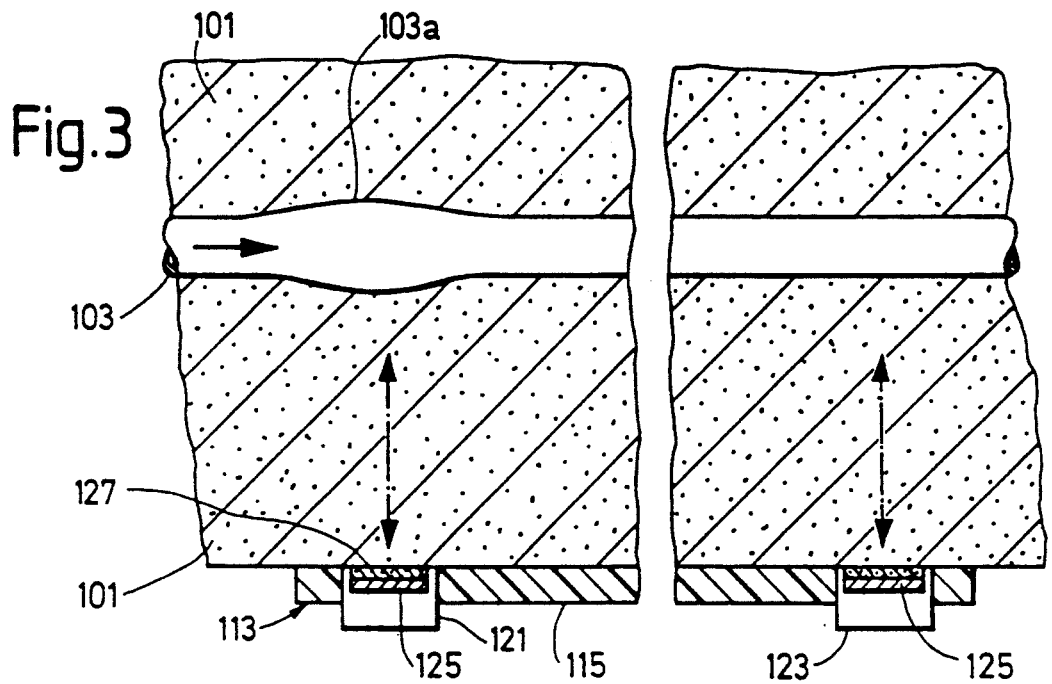
FIG. 3 is a schematic longitudinal sectional view of segments of an arm and sensor means including ultrasound transducers fastened thereto.

FIG. 3 shows a limb 101 having a large artery 103 which has a distended portion 103a caused by the pulsating flowing blood. This distension progresses at the pulse wave velocity. The sensor means 113 disposed, according to FIG. 3, on the exterior of limb 101, include a holder 115 which is releasably fastened to member 101, a first sensor 121 and a second sensor 123. The two sensors 121, 123 are offset relative to one another along the limb analogously to sensors 21 and 23 but are each equipped with at least one ultrasound transducer 125 instead of optoelectronic transducers. Holder 115, when seen in a sectional view at a right angle to the longitudinal direction of arm 101, may be planar and linear or slightly bent on its side intended to lie against the arm. Moreover, the holder may possibly be slightly flexible so that it is able to lie in as good a fit as possible against the surface of arm 101. Each ultrasound transducer 125 has at least one piezoelectric element and is configured in such a way that it serves as a projector and as receiver for ultrasonic waves and is able to convert electrical signals—namely voltage pulses—into ultrasonic waves and to convert scattered back received ultrasonic waves into electrical signals. The transducers and their major project/receive directions, indicated in FIG. 3 by double arrows, and/or their center axes, lie at approximately a right angle to the longitudinal directions of arm 101 and artery 103. An ultrasound coupling agent 127 is disposed between the sides of the piezoelectric elements facing arm 101 and the surface of the arm; it is composed, for example, of a gel-like substance of polyethylene glycol.

The ultrasound transducers 125 of sensors 121, 123 are electrically connected with a supply and detector unit of the electronic circuit means of a display and monitoring unit that is not shown in the drawings. The supply and detector unit is configured in such a way that the ultrasound transducers project pulsed ultrasonic waves into the arm and, between successive pulses, receive ultrasonic waves that are reflected or scattered back. The transducers are arranged on arm 101 in such a way that the ultrasound wave bundles generated by them intersect artery 103. The ultrasonic waves penetrating into large artery 103 are at least in part scattered and/or reflected by the blood flowing through artery 103. The electronic circuit means of the non-illustrated display and monitoring unit are constructed to generate, from the electrical signals generated by sensors 121, 123 when scattered-back ultrasonic waves are received, a value which is a measure of the flow velocity of the blood. The determination of the flow velocity may here be effected, for example, in the same way or similarly to the method disclosed in the publications cited in the introduction and employed for a bundle of ultrasonic waves directed transversely to the flow direction.

The remaining components of the device including sensor means 113 may—unless specified otherwise above—be configured similarly and perform similar functions as defined for device 11.

Figure 4:
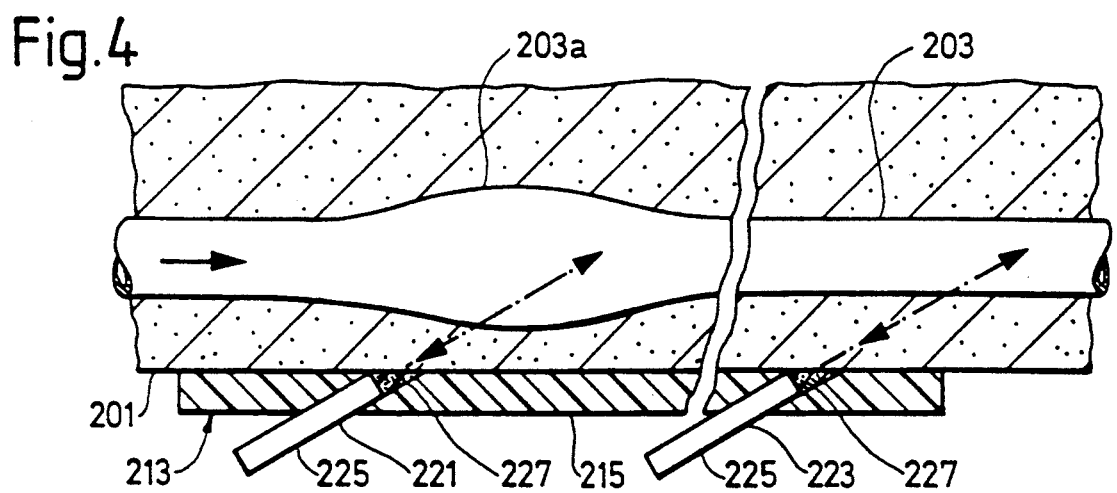
FIG. 4 is a longitudinal sectional view corresponding to FIG. 3 of segments of an arm and sensor means equipped with different ultrasound transducers.

FIG. 4 shows an arm 201 with a large artery 203 which experiences a progressive distension 203a. The sensor means 213 also shown in FIG. 4 include a holder 215 which is releasably fastened to the arm. Two sensors 221, 223 are fastened to the holder, with each sensor including at least one ultrasound transducer 225 which is equipped with a piezoelectric element and serves as a ultrasound source for the pulse-wise emission of ultrasound and as an ultrasound receiver. In deviation from ultrasound transducers 125, ultrasound transducers 225 are arranged in such a way that their major project/receive directions and/or center axes are inclined relative to the longitudinal direction of arm 201 and to the large artery 203, and accordingly include a component that is parallel to the direction of flow of the blood flowing through large artery 203. Between the surface of arm 201 and the sides or ends of transducers 225 facing it, an ultrasound coupling agent 227 is provided, which again may be composed of a polyethylene glycol substance.

The sensors are connected with a non-illustrated display and monitoring unit whose electronic circuit means are configured to determine the flow velocity on the basis of the Doppler effect.

The viscosity of the blood is determined primarily by the number, magnitude and structure of the red and possibly the white blood cells contained in one volume unit of blood. Light and ultrasonic waves are scattered in the blood primarily by its blood cells. Therefore a value which is a measure for the dynamic and/or kinematic viscosity coefficient and/or at least for its change over time can be derived from the scattering of the light and primarily the ultrasonic waves. Accordingly, the devices constructed to detect scattered light or ultrasound may be provided with means and may be configured—as already mentioned—to determine on the basis of this scattering an additional value which is a measure for the viscosity of the blood or at least for a change in its viscosity.

Figure 5:
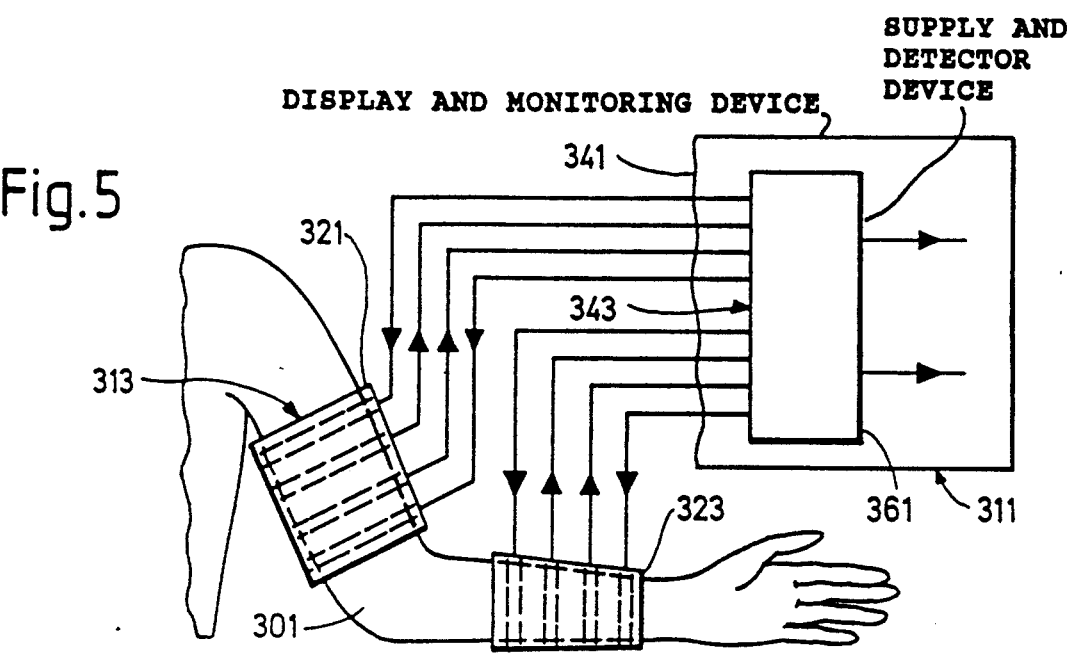
FIG. 5 is a schematic front view of a variant of the sphygmomanometer in which sensor means including two sensors equipped with electrodes for measuring the electrical impedance or admittance are disposed at the arm of a person.
Figure 6:
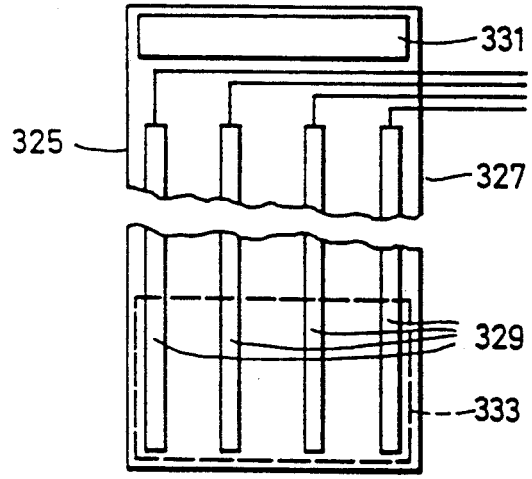
FIG. 6 is a top view to an enlarged scale of the side intended for placement against the arm of the sensor of the device of FIG. 5, which has been removed from the arm.
Figure 7:
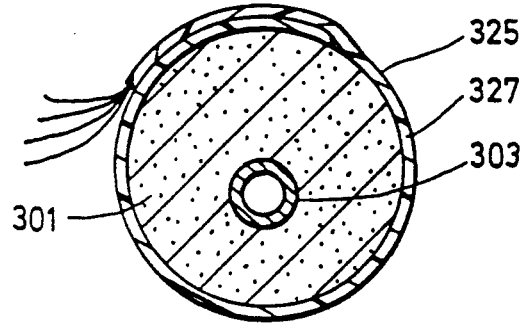
FIG. 7 is a greatly simplified cross-sectional view, to an even larger scale than FIG. 6, of the arm shown in FIG. 5 and a sensor fastened thereto.

FIGS. 5 and 7 show an arm 301 that has a large artery 303. The device 311 also shown in FIG. 5 is configured to determine the blood pressure by detecting the electrical impedance or admittance. Device 311 includes sensor means 313 in the form of two sensors 321, 323 that are releasably fastened to arm 301, and are again spaced from one another along the arm. One sensor, for example, sensor 321, is fastened to the upper arm and the other sensor 323 is fastened to the forearm. Each one of the two sensors, one of which is also shown in FIGS. 6 and 7, is provided with a cuff 325 equipped with a flexible, electrically insulating and possibly slightly elastic band 327 which, on its side facing the arm when in use, is provided with four contact electrodes 329 which are composed of flexible, electrically conductive metal foil strips that are spaced next to one another parallel to the longitudinal direction of the band. Hook-and-loop closure elements 331, 333 are fastened to band 327. In order to perform a measurement, cuff 325 of each sensor is wound around arm 301 in such a manner that contact electrodes 329 lie against the arm and completely enclose it. The overlapping end sections of the cuff are here fastened to one another with the aid of the hook-and-loop closure elements 331, 333.

A display and monitoring unit or device 341 includes electronic circuit means 343. Each contact electrode 329 is connected by way of the conductor of a cable with a supply and detector unit 361 which is part of circuit means 343. The supply and detector unit includes a generator or two generators in order to generate a supply voltage or a supply current at a frequency between 80 kHz and 100 kHz and to feed it to the two outermost electrodes of the two sensors 321, 323. The or each generator may be configured so as to feed current of a constant amplitude into arm 301 for each sensor. The supply and detector unit 361 is further configured to detect the electrical impedance or admittance from the electrical voltages of each sensor that can be picked up between the two inner electrodes of each sensor. Unit 361 may further form, from the component of the impedance or admittance that changes in the rhythm of the pulse beat, a first value which is a measure for the volume. The volume of the blood in a blood vessel is proportional to the cross-sectional area of the blood vessel and is proportional to the square of the inner diameter of the blood vessel. It is primary the volume, flow cross section area and diameter of the large artery, that is, the arteria brachialis of the upper arm and the arteria radialis and the somewhat smaller arteria ulnaris in the forearm, that change during the pulsation of the blood stream. Thus, a measurement of the impedance or admitance also provides a measure for the flow cross section area and for the inner diameter of at least one artery disposed within the measuring region. The electronic circuit means of unit 341 may further be configured to perform an electrical differentiating process in analog or digital form and derive therefrom the first derivative of the volume over time. The derivative or differential quotients determined for the two measuring regions then each provide a measure for the flow quantity of the arterial blood in the arm regions covered by the two sensors. Device 311 thus enables the determination in the two measuring regions of a first value which is a relative measure for the volume and/or the flow quantity of the blood and/or the passage cross section area and/or the inner diameter of at least one blood vessel. For further general principles of this type of measuring, reference is made to the publications cited in the introduction.

The supply and detector unit 361 is connected with a non-illustrated evaluation unit which, similar to evaluation unit 65, is able to determine the pulse wave velocity from the time shift in the first pulsating value picked up by the two sensors. The evaluation unit that is part of the electronic circuit means 343 may additionally be configured to determine the blood pressure from at least one of the variants measured as the first value in at least one measuring region for the pulse wave velocity $c_{pw}$ and the calibration values, in a manner analogous to the determination of the blood pressure from v and $c_{pw}$ in evaluation unit 65. In the case where the flow quantity or the flow cross section area proportional thereto is determined as the first value and if it is further assumed that the blood vessels have rigid walls, the blood pressure would, by the way, according to Equation (5), be proportional to the ratio of $Q/r^4$.

Figure 8:
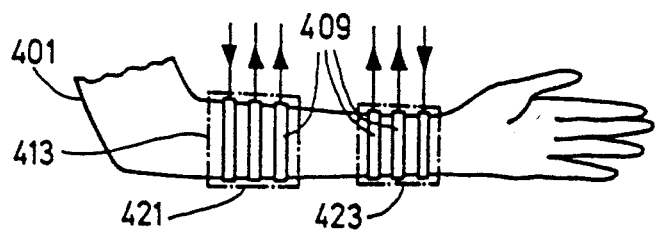
FIG. 8 is a schematic representation of a variant of the sensor means disposed at an arm and including electrodes for measuring the electrical impedance or admittance.

Sensor means 413, including two sensors 421, 423 for measuring the electrical impedance or admittance, are releasably fastened to the arm 401 shown in FIG. 8. Sensor means 413 differ from sensor means 313 in that altogether they include only a total of six contact electrodes 409. During measuring, a high frequency alternating current common to both sensors is introduced into the arm at the two outermost electrodes 409. Otherwise, the two sensors each include a cuff, indicated in dash-dot lines, but could also have a common cuff.

The devices described in connection with FIGS. 5 to 8 could possibly be modified by replacing a few or all contact electrodes with electrodes that are electrically insulated against the body surface and which enclose the arm or some other body segment. Each one of these electrodes that are attached to the body in an electrically insulated manner then in a way constitutes a coil-like antenna which likewise permits a measurement of the impedance or admittance to be made.

As already mentioned in the introduction, the device could also be configured to measure as the first value the diameter of an artery, preferably of a large artery, while employing ultrasound reflection. In that case, the device would include, for example, sensors which are provided, similarly to sensors 121, 123, with ultrasound transducers 125. The electronic circuit means could then be configured to generate electrical signals on the basis of the reflection of ultrasonic waves at at least one section of the artery wall and preferably at two approximately diametrically opposed sections of the artery wall. These electrical signals then provide a measure in at the two sensors for the momentary values and/or changes over time of the inner or outer or average diameter or other cross-sectional dimensions and thus also of the flow cross section areas. The pulse wave velocity can then be determined from the shift over time that results at the two sensors between periodic time changes in synchronism with the pulse beat. Moreover, the blood pressure can be determined from the measured values and from the fed-in calibration values. This can be done in a similar manner as described for the device 11 shown in FIGS. 1 and 2 which measures flow velocity.

In the above-described embodiments of the device according to the invention, two identical sensors are provided which are offset along an artery. As already mentioned in the introduction, it is, however, also possible to provide sensor means which are equipped with only a single sensor for measuring the first value.

Figure 9:
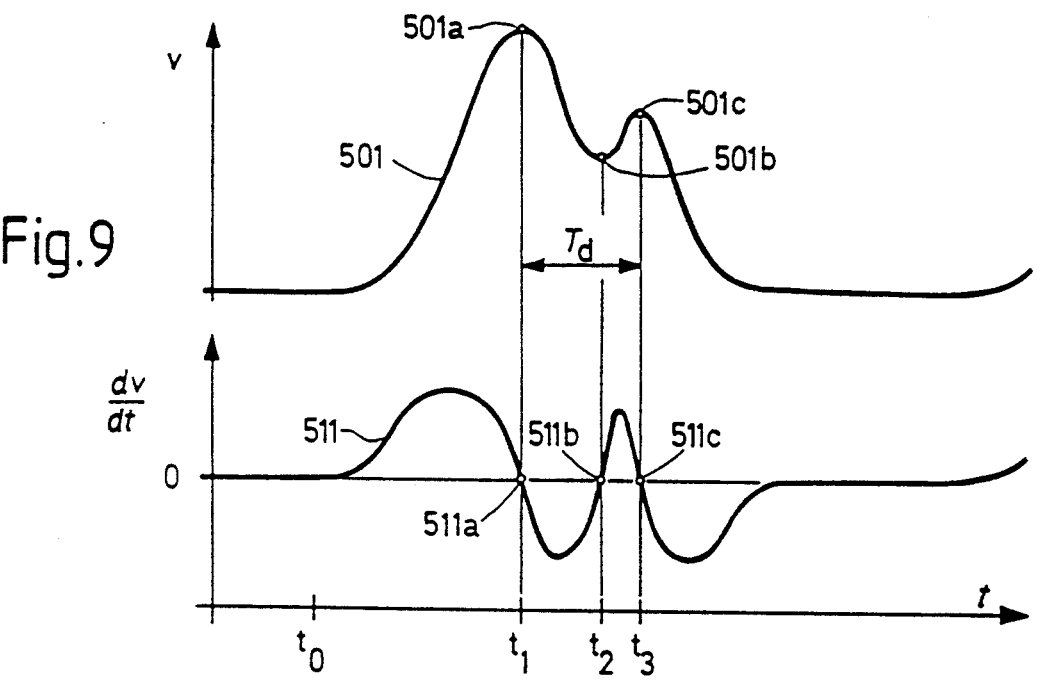
FIG. 9 is a diagram illustrating the determination of the pulse wave velocity on the basis of reflected pulse waves.

For example, the pulse wave velocity can then be determined—as also discussed in the introduction—from the influence on the time curve that is a result of a reflection of the pulse waves for the variable measured as the first value. This will now be explained in connection with FIG. 9 for the case where one sensor and electronic circuit means are provided to measure as the first value the flow velocity v of the blood with the aid of light or ultrasound. FIG. 9 includes two partial diagrams that have a common abscissa on which the time t is plotted. In the upper partial diagram, the flow velocity v is plotted on the ordinate. Curve 501 of the upper partial diagram shows the somewhat schematized curve of the flow velocity of the blood flowing through an artery during approximately one pulse period. In the lower partial diagram, the differential quotient dv/dt is plotted on the ordinate. Curve 511 of the lower partial diagram correspondingly shows—likewise in schematic form—the curve of the mentioned differential quotient. According to curve 501, the flow velocity v begins to rise during a cardiac cycle, starting from a minimum value at time $t_0$, and at time $t_1$ reaches a primary maximum 501a which at least approximately coincides with the occurrence of the systolic blood pressure. The flow velocity v then drops, reaches a relative intermediate minimum 501b at time $t_2$, then rises again and reaches a secondary maximum 501c at time $t_3$ at which the dicrotic notch occurs in the blood pressure curve. Then the flow velocity drops again to approximately the initial minimum value. The curve 511 representing the course of differential quotient dv/dt correspondingly experiences a zero passages 511a, 511b, 511c, at times $t_1$, $t_2$, $t_3$, repectively, passing through the zero line from the top to the bottom at zero passages 511a and 511c and from the bottom to the top at zero passage 511b.

As discussed in the introduction, the dicrotic notch and thus the secondary maximum 501c associated therewith is caused by the interference of the primary pulse wave moving away from the heart with a reflected pulse wave. The time difference $T_d$ between the two maxima 501a and 501c therefore is a measure for the travel time of the reflected pulse waves and thus for the pulse wave velocity.

The electronic circuit means and particularly the evaluation unit of the device provided to determine the pulse wave velocity on the basis of pulse wave reflection are configured to form from the flow velocity measured as the first value the first derivation over time—that is, the differential quotient dv/dt—and preferably also the second derivative over time, that is the differential quotient $d^2v/dt^2$. This differentiation may be effected electrically in analog form with the aid of a differentiating circuit, or in digital form with the aid of a microprocessor computer. The circuit means then may identify times $t_1$ and $t_3$ on the basis of the differential quotients and measure the time difference $T_d$. The time difference $T_d$ or a value linked thereto, for example its reciprocal value, then constitutes a measure for the second value which provides the pulse wave velocity and whose value is represented in the form of a digital or analog electrical signal.

If instead of the flow velocity v, another one of the variables in question is measured as the first value, the value providing a measure for the pulse wave velocity can be determined in a similar manner as discussed in connection with FIG. 9 for flow velocity v.

Figure 10:
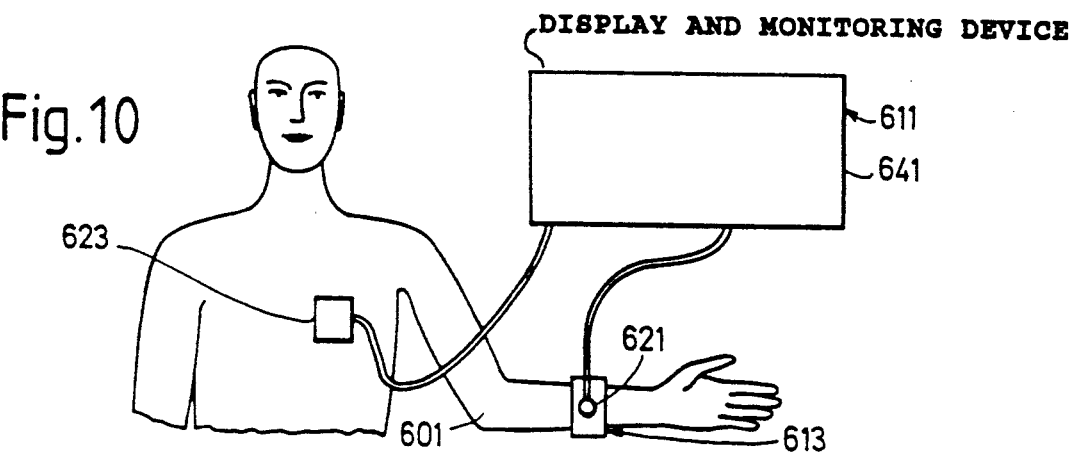
FIG. 10 is a schematic representation of a person and a sphygmomanometer configured to determine the pulse wave velocity by detecting a cardiac muscle current.

FIG. 10 shows the arm 601 of a person and a device for measuring the blood pressure, here marked 611. The sensor means 613 of device 611 include only a single sensor 621 that is releasably fastened to arm 601. This sensor includes, for example, transducers serving to measure the flow velocity by means of light or ultrasound, but could also be configured to determine a variable usable as the first value from a different measurement, for example an impedance or admittance measurement. However, sensor means 613 also include contact electrodes that are fastened, for example, to the chest of the person being examined and together form at least one sensor 623. Sensor 621 and the contact electrodes of sensor 623 are connected with a display and monitoring unit or device 641 by way of cables. The electronic circuit means of this device are configured to pick up, together with the contact electrodes of sensor 623, at least one current of the cardiac muscle, similarly to the procedures in electrocardiography, and to determine the so-called R wave of the cardiogram at which the systole—that is, the contraction of the cardiac muscle—and the expulsion of blood from the heart occur. Unit 641 may further determine the time difference between the R wave and the time at which the flow velocity of the blood in arm 601 or the other first value measured by sensor 621 reaches its maximum value during a pulse period. This time difference and its change, or a value derived from this time difference and its change, then provide a measure for the pulse wave velocity and its change.

The devices and methods for operating them may also be modified in a different respect. In this connection, particular features of various described devices and methods may be combined with one another. For example, sensors may be provided which, like sensors 21, 23, include light sources and light receivers but are arranged analogously to sensors 121, 123 which are equipped with an ultrasound transducer in order to beam light into the arm in a direction at an angle to the arm so that then an optical Doppler effect measurement can be performed.

If a measurement is to be made by means of a bundle of light or ultrasound beams that intersect a large artery, sensors may further be provided which each include several identical transducers that are offset relative to one another transversely to the mentioned artery. If such a sensor is fastened, for example, to the arm including the mentioned large artery, it is possible without accurate positioning of the sensor for the center axis of the radiation from one of its transducers to intersect the large artery. The electronic circuit means may then be configured so as to automatically select during measuring the transducer signal that is modulated most by the pulse for further processing.

The described devices and methods according to the invention all have the advantage that they permit long-term, continuous or at least quasi-continuous—for example, for every cardiac cycle—measurements of the blood pressure, with the person, or possibly the animal, being examined being only relatively slightly. It is here of particular advantage that for calibration only a one-time calibration measurement, or very few calibration measurements, need to be performed according to the Riva-Rocci method and that during the major portion of the measuring period, it is not necessary to inflate and deflate a cuff.

The blood pressure measuring and pulse rate measuring method performed with the use of one of the described devices may be employed in therapy for long-term monitoring and also, for example, for commercial examinations performed in hospitals and possibly in medical offices to determine a patient's general physical condition, in human as well as in veterinary medical research and in the development and testing of medicinal preparations.

What is claimed is:

1. A device for measuring blood pressure of a living body having a pulse beat with a rhythm and producing a pulse wave propagating with a pulse wave velocity, comprising:
   sensor means for generating sensor data when the sensor means is attached to the living body; and
   electronic circuit means for determining the blood pressure of the living body from the sensor data, the electronic circuit means including
      first means, responsive to the sensor data, for determining a measurement value which is a measure for a first variable that can assume a plurality of first variable values, the first variable changing over time in the rhythm of the pulse beat and being correlated with at least one of the blood pressure and a change in the blood pressure,
      second means, responsive to the sensor data, for determining another measurement value which is a measure for a second variable that can assume a plurality of second variable values, the second variable being correlated with at least one of the pulse wave velocity and a change in the pulse wave velocity,
      third means for receiving calibration data during a calibration procedure and for storing at least one constant determined by the calibration data,
      fourth means for determining a function value on the basis of the measurement value for the first variable and the measurement value for the second variable; and
      fifth means for using the function value and said at least one constant to determine a value for the blood pressure.

2. A device according to claim 1, wherein the first variable is selected from the group consisting of the momentary flow velocity of blood through at least one artery in a measuring region, a change in the flow velocity of blood through at least one artery in the measuring region, the blood flow quantity through at least one artery in the metering region, the volume of the blood in at least one artery in the measuring region, a cross-sectional dimension of at least one artery in the measuring region, and the cross section area of at least one artery in the measuring region, as they occur in synchronism with the pulse beat.

3. A device according to claim 1, wherein the sensor means comprises means for sending waves into a measuring region of the body including at least one arterial blood vessel and for receiving waves scattered by blood in the at least one arterial blood vessel, wherein the first variable is one of the flow velocity of blood through the at least one arterial blood vessel in the measuring region and the flow quantity of blood through the at least one arterial blood vessel in the measuring region, and wherein the first means comprises means for determining from the scattered waves a measurement value for one of the flow velocity and flow quantity of blood flowing through the at least one arterial blood vessel in the measuring region.

4. A device according to claim 1, wherein the sensor means comprises means for sending lightwaves into a measuring region of the body and for converting scattered-back lightwaves into at least one electrical signal.

5. A device according to claim 4, wherein the means for sensing lightwaves comprises at least one light source which generates lightwaves whose wavelength is at least 700 nm and at most 1200 nm.

6. A device according to claim 1, wherein the sensor means comprises at least one ultrasound transducer which sends ultrasonic waves into at least one measuring region of the body and which converts scattered-back ultrasonic waves into at least one electrical signal.

7. A device according to claim 1, wherein the sensor means comprises electrodes, wherein the first variable is selected from the group consisting of the volume of blood in at least one artery in a measuring region, the blood flow quantity through at least one artery in the measuring region, the cross-sectional area of at least one artery in the measuring region, and the inner diameter of at least one artery in the measuring region, and wherein the first means comprises means for determining one of the electrical impedance, admittance, change in the impedance over time, and change in the admittance over time in the measuring region and for forming therefrom, as the measurement value for the first variable, a value for one of the volume of blood in at least one artery in the measuring region, the blood flow quantity through at least one artery in the measuring region, the cross-sectional area of at least one artery in the measurement region, and the inner diameter of at least one artery in the measuring region.

8. A device according to claim 1, wherein the sensor means comprises at least one ultrasound transducer for sending ultrasonic waves into at least one measuring region of the body and which receives reflected ultrasonic waves from at least one wall section of an artery, wherein the first variable is selected from the group consisting of the diameter of the artery, a change in the diameter of the artery, the cross-sectional area of the artery, and a change in the cross-sectional area of the artery, and wherein the first means comprises means for determining, as the measurement value of the first variable, a value for one of the diameter of the artery, the cross-sectional area of the artery, a change in the diameter of the artery, and a change in the cross-sectional area of the artery.

9. A device according to claim 1, wherein the sensor means comprises two sensors for determining, in two measuring regions which are spaced from one another along an artery, changes over time which occur periodically in the rhythm of the pulse beat in the first variable, wherein the second variable is the pulse wave velocity, and wherein the second means comprises means for determining, from a time shift between the periodic time changes in said first variable as determined by the two sensors, a value for the pulse wave velocity as the measurement value of the second variable.

10. A device according to claim 1, wherein the second variable is the pulse wave velocity, and wherein the second means comprises means for identifying a primary extreme occurring during a pulse period and corresponding to the systolic blood pressure as well as an additional extreme caused by interference between a pulse wave moving away from the heart and a reflected pulse wave and to determine a time or phase shift between the two extremes and to form therefrom a value constituting a measure for the pulse wave velocity as the measurement value for the second variable.

11. A device according to claim 1, wherein the sensor means is disposed at a measuring location that is remote from the cardiac muscle of the living body, wherein a graph of the first variable as a function of time has a predetermined feature occurring during each pulse period, further comprising additional sensor means for determining an electrical current associated with the cardiac muscle, the electrical current associated with the cardiac muscle changing over time and having a predetermined feature occurring during each pulse period in the change over time, and wherein the second means is responsive to the electrical current associated with the cardiac muscle and comprises means for determining the measurement value for the second variable on the basis of a time shaft between the occurrence of the predetermined feature occurring during each pulse period in the change over time of the electrical current associated with the cardiac muscle and the predetermined feature occurring during each pulse period in the graph of the variable as a function of time.

12. A device according to claim 1, wherein the first means comprises means for determining a measurement value for the first variable repeatedly for the same living body, wherein the second means comprises means for determining a measurement value for the second variable repeatedly for the same living body, wherein the fourth means comprises means for determining function values repeatedly, and wherein the fifth means comprises means for repeatedly using the function values and said at least one constant to repeatedly determine at least one of the systolic and diastolic blood pressure of the same living body.

13. A device according to claim 12, wherein the means for repeatedly using function values and said at least one constant to repeatedly determine at least one of the systolic and diastolic blood pressure of the body comprises means for determining at least one of the systolic and diastolic blood pressure at each heart beat of the body.

14. A device according to claim 1, wherein the calibration procedure is conducted on the same living body and the calibration data comprises at least one calibration blood pressure value measured during the calibration procedure, and wherein the third means further comprises means for determining the at least one constant from the at least one calibration blood pressure value.

15. A device according to claim 1, wherein the calibration procedure is conducted on the same living body, wherein the third means comprises means for storing two constants determined by the calibration data, and wherein the fifth means comprises means for multiplying one of the constants by the function value to determine a product and for adding the other constant to the product to determine the value for the blood pressure.

16. A device according to claim 1, wherein the fourth means comprises means for storing a table that associates a function value to every pair of a first variable value and a second variable value, and means for reading from the table, for each pair of a first variable value and a second variable value, an associated function value.

17. A device for measuring blood pressure of a living body having a pulse beat with a rhythm and producing a pulse wave propagating with a pulse wave velocity, comprising:
sensor means for generating sensor data when the sensor means is attached to the living body; and
electronic circuit means for determining the blood pressure of the living body from the sensor data, the electronic circuit means including
first means, responsive to the sensor data, for determining a measurement value which is a measure for a first variable that can assume a plurality of first variable values, the first variable changing over time in the rhythm of the pulse beat and being correlated with at least one of the blood pressure and a change in the blood pressure,
second means, responsive to the sensor data, for determining another measurement value which is a measure for a second variable that can assume a plurality of second variable values, the second variable being correlated with at least one of the pulse wave velocity and a change in the pulse wave velocity,
third means for receiving calibration data during a calibration procedure and for storing at least one constant determined by the calibration data,
fourth means for storing a table which associates table values with variable values, including at least the second variable values,
fifth means for selecting one of the table values on the basis of the measurement value for the second variable to provide a selected table value,
sixth means for multiplying the selected table value by one of the measurement value for the first variable, a table value associated by the table with the measurement value for the first variable, and a value computed from the measurement value for the first variable by a predetermined equation to provide a product value, and
seventh means for using the product value and said at least one constant to determine a value for the blood pressure.

18. A device according to claim 17, wherein the first means comprises means for determining a measurement value for the first variable repeatedly for the same living body, wherein the second means comprises means for determining a measurement value for the second variable repeatedly for the same living body, wherein the fifth means comprises means for providing selected table values repeatedly, wherein the sixth means comprises means for providing product values repeatedly, and wherein the seventh means comprises means for repeatedly determining a value for at least one of the systolic and diastolic blood pressure for the same living body.

19. A device according to claim 17, wherein the calibration procedure is conducted on the same living body and the calibration data comprises at least one calibration blood pressure value measured during the calibration procedure, and wherein the third means further comprises means for determining the at least one constant from the at least one calibration blood pressure value.

20. A device according to claim 17, wherein the calibration procedure is conducted on the same living body and the third means comprises means for storing two constants determined by the calibration data, and wherein the seventh means comprises means for multiplying the product value by one of the constants to obtain a resulting value and for adding the resulting value to the other constant.

21. A device for measuring blood pressure of a living body having a pulse beat with a rhythm and producing a pulse wave propagating with a pulse wave velocity, comprising:
sensor means for generating sensor data when the sensor means is attached to the living body; and
electronic circuit means for determining the blood pressure of the living body from the sensor data, the electronic circuit means including first means, responsive to the sensor data, for determining a measurement value which is a measure for a first variable that changes over time in the rhythm of the pulse beat and is correlated with at least one of the blood pressure and a change in the blood pressure, second means, responsive to the sensor data, for determining another measurement value which is a measure for a second variable that is correlated with at least one of the pulse wave velocity and a change in the pulse wave velocity, third means for receiving calibration data during a calibration procedure and for storing at least one constant determined by the calibration data, and fourth means for computing a blood pressure value using an equation expressing the blood pressure explicitly in dependence on the measurement value for the first variable, the measurement value for the second variable, and the at least one constant.

22. A device according to claim 21, wherein the calibration procedure is conducted on the same living body and the third means comprises means for storing two constants determined by the calibration data, and wherein the fourth means comprises means for computing a first function value from the measurement value for the first variable, means for computing a second function value from the measurement value for the second variable, means for multiplying one of the constants by the first function value and by the second function value to provide a product, and means for adding the other constant by the product.

23. A method of determining the blood pressure of a living body using a device which includes sensor means for generating sensor data and electronic circuit means for determining the blood pressure of the living body from the sensor data, the living body having a pulse beat with a rhythm and producing a pulse wave propagating with a pulse wave velocity, said method comprising the steps of:

(a) disposing the sensor means on the body at at least one measuring region that includes at least one arterial blood vessel;

(b) using the electronic circuit means to repeatedly determine, in response to the sensor data, a measurement value which is a measure for a first variable that can assume a plurality of first variable values, the first variable periodically changing over time in the rhythm of the pulse beat;

(c) using the electronic circuit means to repeatedly determine, in response to the sensor data, another measurement value which is a measure for a second variable that can assume a plurality of second variable values, the second variable being the pulse wave velocity;

(d) measuring the blood pressure of the body during a calibration procedure;

(e) storing, in the electronic circuit means, at least one constant determined by the calibration procedure;

(f) using the electronic circuit means to repeatedly determine a function value on the basis of the repeatedly-determined measurement value for the first variable and the repeatedly-determined measurement value for the second variable; and (g) using the repeatedly-determined function value and the at least one constant in the electronic circuit means to provide blood pressure values.

24. A method according to claim 23, wherein a table containing a plurality of function values is stored in the electronic circuit means, the table associating each function value with a first variable value and a second variable value, and wherein step (f) comprises selecting one of the function values contained in the table on the basis of the measurement value for the first variable and the measurement value for the second variable.

25. A method according to claim 23, wherein step (d) comprises the steps of temporarily fastening a cuff defining a cavity to the body inflating and deflating the cuff; measuring the pressure in the cavity; determining the at least one calibration value; and removing the cuff.

* * * * *